United States Patent [19]

Munder

[11] Patent Number: 4,778,788

[45] Date of Patent: Oct. 18, 1988

[54] AGENT AGAINST MULTIPLE SCLEROSIS

[75] Inventor: Paul G. Munder, Gundelfingen, Fed. Rep. of Germany

[73] Assignee: Max-Planck-Gesellschaft Zur Foerderung der Wissenschaften, Goettingen, Fed. Rep. of Germany

[21] Appl. No.: 46,875

[22] PCT Filed: Aug. 28, 1986

[86] PCT No.: PCT/EP86/00506

§ 371 Date: May 21, 1987

§ 102(e) Date: May 21, 1987

[87] PCT Pub. No.: WO87/01257

PCT Pub. Date: Mar. 12, 1987

[30] Foreign Application Priority Data

Aug. 28, 1985 [DE] Fed. Rep. of Germany ....... 3530767

[51] Int. Cl.⁴ ............................................. A61U 31/685
[52] U.S. Cl. ....................................................... 514/77
[58] Field of Search .......................... 514/140, 141, 77

*Primary Examiner*—Stanley J. Friedman
*Attorney, Agent, or Firm*—Felfe & Lynch

[57] ABSTRACT

The use of a compound having the general formula I

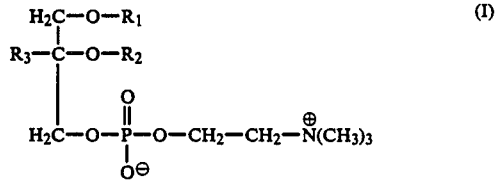

in which $R_1$ is alkyl having from 12 to 18 carbon atoms, $R_2$ is alkyl having from 1 to 8 carbon atoms, and $R_3$ is H or alkyl having from 1 to 3 carbon atoms, is described as an agent against multiple sclerosis.

14 Claims, 1 Drawing Sheet

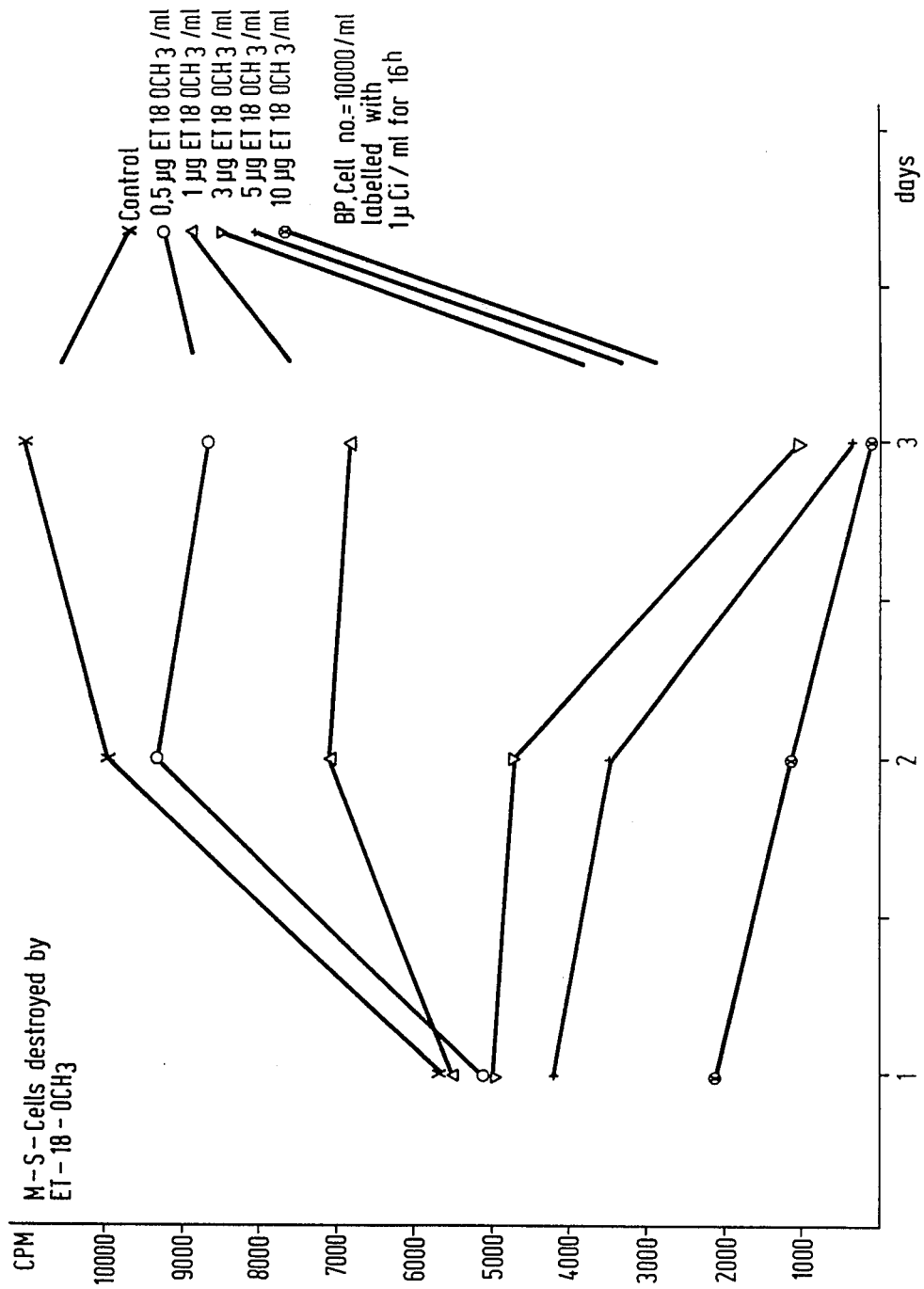

AGENT AGAINST MULTIPLE SCLEROSIS

The invention concerns the use of compounds of the lysolecithine type as an agent against multiple sclerosis.

In DE-OS 20 09 342 and DE-OS 20 09 343, the use of synthetic lysolecithine compounds is described to increase resistance and an immunological adjuvants. Moreover, from DE-OS 26 19 686 the effectiveness of such compounds as antitumor agents is known. In addition, after the application of lysophosphatides there is a formation of activated cells which are capable of increasing the resistance of the body to harmful influences.

It has now surprisingly been found that lysolecithine analogues having the general formula I demonstrate good effectiveness in the treatment of multiple sclerosis.

The subject of the invention is therefore the use of a compound of the general formula I

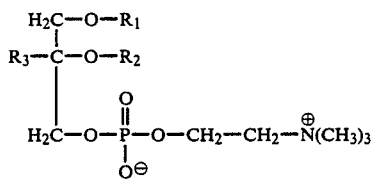

in which $R_1$ is alkyl having from 12 to 18, and in particular from 16 to 18 carbon atoms, $R_2$ is alkyl having from 1 to 8 carbon atoms, $R_3$ is H or alkyl having from 1 to 3 carbon atoms, as an agent against multiple sclerosis.

An alkyl group $R_1$, $R_2$ and/or $R_3$ can be branched, and is prefereably straight-chained.

In a compound of the general formula I, $R_2$ is preferably an alkyl radical with from 1 to 3 carbon atoms, and especially methyl, and/or $R_3$ is preferably H.

Preferred compounds are, in particular, the compound of formula I where $R_1$=n-hexadecyl, and $R_2$=methyl and where $R_3$=H (compound II) and primarily the compound of the formula I where $R_1$=n-octadecyl, and $R_2$=methyl and $R_3$=H (compound III).

The preparation of the compounds according to formula I can be performed in one of the ways which have been described in the literature; compare, for example, D. Arnold et al, Liebig's Ann. Chem. 709, 234–239 (1967); H. U. Weltzien and O. Westphal, Liebig's Ann. Chem. 709, 240–243 (1967); and H. Eibl and O. Westphal, Liebig's Ann. Chem. 709, 244–247 (1967).

Multiple sclerosis (MS), one of the most frequent nerve diseases, is an autoimmune illness in which T-lymphocytes penetrate into the nerve substance decompose the myelin there.

MS can be artificially generated in animal tests, in that the so-called basic protein is extracted from myelin, and this basic protein is injected into test animals (mice) with complete Freund adjuvant. After from 5 to 7 days, lymphocytes are extracted from the animals. The lymphocytes which are extracted from the animal can initiate MS when they are administered to a test animal, in which process at least $10^6$-T-cells per animal must be administered (compare Ben-Nun A., Wekerle and Cohen I. R. The rapid isolation of clonable antigen specific T-lymphocyte capable of mediating autoimmune encephalomyletitis Eur. J. Immunology (1981), 11 195).

If now a compound according to the invention having general formula I, for example the compound III, is administered to the animals, the MS symptoms can be removed. Hence it can be concluded that the compounds in accordance with the invention evidently de-activate those T-cell clones in some way which have developed the specificity which causes the MS symptoms against myelin or basic protein.

Moreover, in the case of humans suffering from MS, after the administration of the compound III, a clear improvement of the MS symptoms was observed: in the case of oral administration (solution of compound III in liquids containing lipoprotein, for example in milk), after a daily administration of 200 μg for a period of several weeks and subsequent transition to administration only every second day of 200 μg, there was complete freedom from the complaint which could be maintained, which, for example, was expressed in the capability for completely normal motion, driving automobiles etc.

The application of the substances according to the invention can, as a rule, be carried out in the conventional manner, for example by means of the administration of such compounds as antitumor agents, i.e. for example intravenously, perorally or as an infusion; oral administration is, as a rule, the preferred type of application for reasons of expediency and in the event of application being necessary over a longer period.

The form of administration (pharmaceutical preparation) can contain the conventional additives, such as the usual pharmaceutical ancillary processing agents and/or dilutant agents, and optionally other active ingredients, to the extent that they have no undesirable side effects with the other components and that they are suitable to reinforce the therapy.

As a rule, the effective dose of the compound according to the invention amounts to between 1 and 10 μg/kg of body weight per day, which in the case of administration to human beings corresponds to a dose of approximately 100 μg to 500 μg per day; preferably, the dose amounts to from 150 to 300 μg per day, the amount and frequency of the administration, however, being oriented towards the general state of health of the patients and towards the gravity of the illness.

EXAMPLE 1:

A patient, in the case of whom multiple sclerosis had been diagnosed four years earlier and who suffered from a spastic paresis of the right leg and from a feeling of dizziness, had been treated for years on end with cortisone and imurek. In addition, physiotherapeutic exercises were carried out. The result was a slow improvement, but the patient could only move for a short distance for about 20 minutes. In addition, there was a strong dependency on the weather in her general health. After two years there was a renewed attack. The result was disturbances to the sensitisation in both arms and the right leg, difficulties in writing, strong uncertainty in walking in the right leg, a marked reduction in the distance walked, so that she was practically unable to leave her appartment any more. Moreover, there were temporarily disturbances in her eyesight and she suffered from the sensation of dizziness. Despite taking higher cortisone doses for 5 months, no improvement was observed. At this stage the administration of compound III, which will be designated ET-18-OCH$_3$, was commenced. Each day 200 μg of this compound, dissolved in milk, were administered. After 14 days of this treatment it was possible to end the cortisone therapy.

The disturbances in sensitisation and eyesight disappeared. The patient continued to be given 200 μg of the medicine ET-18-OCH₃. This therapy was then continued for a further 18 months. With small pauses, the distance covered now amounts to approximately 4 hours. Climatic changes, such as residence on a lake or in the mountains no longer adversely affect her general health. No observable side effects have appeared. The patient is healthy again and is capable of working.

EXAMPLE 2:

The effect of various doses of ET-18-OCH₃ on MS cells was investigated. Autoaggressive lymphocytes, which cause multiple sclerosis were extracted from rats (Ben-Nun A., Wekerle and Cohen I. R. The rapid isolation of clonable antigen specific T-lymphocyte capable of mediating autoimmune encephalomyletitis Eur. J. Immunology (1981), 11 195). These cells were cultivated in the manner known per se and were treated with ET-18-OCH₃. The number of cells was determined after 1, 2 and 3 days. Parallel thereto labelling was carried out by the incorporation of ³H-thymidine. The results can be seen in FIG. 1. It has been demonstrated that by treatment using ET-18-OCH₃, MS cells are destroyed. In the case of doses from 3 μg/ml to 10 μg/ml, after 3 days practically all the MS cells are destroyed.

I claim:

1. A method of treating multiple sclerosis in a subject comprising administering to said subject with multiple sclerosis an effective amount of a compound having the formula

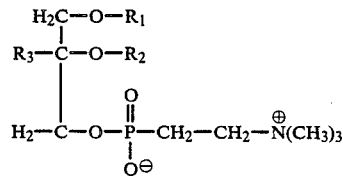

wherein $R_1$ is alkyl having 12 to 18 carbon atoms, $R_2$ is alkyl having from 1 to 8 carbon atoms and $R_3$ is H or alkyl having from 1 to 3 carbon atoms.

2. Method as in claim 1, wherein $R_2$ is an alkyl group having from 1 to 3 carbon atoms.

3. Method as in claim 1 wherein said compound is:

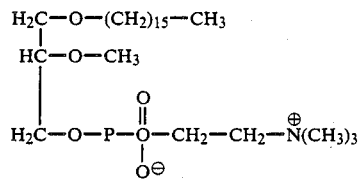

4. Method as in claim 1 wherein said compound is:

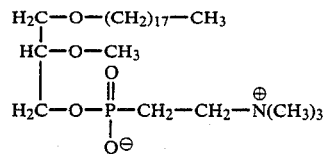

5. Method as in claim 1, wherein $R_1$ is alkyl of 16 to 18 carbon atoms.

6. Method as in claim 1, wherein $R_3$ is H.

7. Method as in claim 1, wherein $R_3$ is alkyl of 1 to 3 carbon atoms.

8. Method as in claim 1, wherein at least one of $R_1$, $R_2$ and $R_3$ is straight chained.

9. Method as in claim 1, wherein at least one of $R_1$, $R_2$ and $R_3$ is branched.

10. Method as in claim 1, wherein said compound is administered in intravenous, oral, or infusion form.

11. Method as in claim 1, wherein said compound is administered in oral form.

12. Method as in claim 1, wherein said compound is administered in an amount ranging from 1 μg to 10 μg per kilogram of body weight of said subject.

13. Method as in claim 1, wherein said compound is administered in an amount ranging from 100 μg to 500 μg per day.

14. Method as in claim 1, wherein said compound is administered in an amount from 150 μg to 300 μg per day.

* * * * *